US011213620B2

(12) United States Patent
Nekouzadeh et al.

(10) Patent No.: US 11,213,620 B2
(45) Date of Patent: Jan. 4, 2022

(54) DRUG DELIVERY DEVICES WITH PARTIAL DRUG DELIVERY MEMBER RETRACTION

(71) Applicant: AMGEN INC., Thousand Oaks, CA (US)

(72) Inventors: Ali Nekouzadeh, Simi Valley, CA (US); Carl Conrath, Thousand Oaks, CA (US); Scott Robert Gibson, Simi Valley, CA (US); Basel Hasan Taha, Simi Valley, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 17/278,618

(22) PCT Filed: Oct. 7, 2019

(86) PCT No.: PCT/US2019/055010
§ 371 (c)(1),
(2) Date: Mar. 22, 2021

(87) PCT Pub. No.: WO2020/091956
PCT Pub. Date: May 7, 2020

(65) Prior Publication Data
US 2021/0308376 A1    Oct. 7, 2021

Related U.S. Application Data

(60) Provisional application No. 62/754,402, filed on Nov. 1, 2018.

(51) Int. Cl.
*A61M 5/20* (2006.01)
*A61M 5/172* (2006.01)
(Continued)

(52) U.S. Cl.
CPC ............ *A61M 5/172* (2013.01); *A61M 5/145* (2013.01); *A61M 5/14248* (2013.01);
(Continued)

(58) Field of Classification Search
CPC ........ A61M 5/1723; A61M 2005/1585; A61M 2005/1583; A61M 2005/14252; A61M 2205/332
See application file for complete search history.

(56) References Cited

U.S. PATENT DOCUMENTS 3,316,909 A    5/1967  Cowley
3,720,211 A    3/1973  Kyrias
(Continued)

FOREIGN PATENT DOCUMENTS

GB    2550924 A    12/2017
KR    101776258 B1    9/2017
(Continued)

OTHER PUBLICATIONS

International Search Report and Written Opinion for International Patent Application No. PCT/US2019/055010, dated Jan. 20, 2020.
(Continued)

*Primary Examiner* — Laura A Bouchelle
(74) *Attorney, Agent, or Firm* — Marshall, Gerstein & Borun LLP (57) ABSTRACT

Methods, devices, and components are provided to reduce tissue resistive pressure during a subcutaneous drug delivery operation by increasing the size of the injection cavity by partially retracting the drug delivery member after inserting the drug delivery member to a subcutaneous position. The drug delivery devices described herein include a magnetic actuator operably coupled to a primary container assembly including a drug delivery member. Power can be selectively provided to the magnetic actuator by a controller to retract
(Continued)

the drug delivery member a predetermined distance to relieve pressure in an injection cavity in a patient. A force sensor can provide the controller with a drug delivery member insertion force. The controller can then estimate a tissue resistive pressure based on the drug delivery member insertion force and determine the predetermined distance for the drug delivery member retraction based on the tissue resistive pressure.

10 Claims, 2 Drawing Sheets

(51) Int. Cl.
*A61M 5/145* (2006.01)
*A61M 5/142* (2006.01)

(52) U.S. Cl.
CPC ..... *A61M 5/20* (2013.01); *A61M 2005/14252* (2013.01); *A61M 2005/206* (2013.01); *A61M 2205/332* (2013.01); *A61M 2205/52* (2013.01)

(56) References Cited

U.S. PATENT DOCUMENTS

| | | | |
|---|---|---|---|
| 3,797,489 A | | 3/1974 | Sarnoff |
| 4,699,612 A | | 10/1987 | Hamacher |
| 6,478,768 B1 | | 11/2002 | Kneer |
| 7,637,891 B2 * | | 12/2009 | Wall ............... A61K 9/0019 |
| | | | 604/131 |
| 8,795,230 B2 | | 8/2014 | Schoonmaker et al. |
| 9,248,240 B2 * | | 2/2016 | Casey ............... A61M 5/3287 |
| 9,814,840 B2 | | 11/2017 | Cowe et al. |
| 9,844,635 B2 | | 12/2017 | Schoonmaker et al. |
| 9,849,252 B2 | | 12/2017 | Armes |
| 2006/0122555 A1 * | | 6/2006 | Hochman ......... A61M 5/16854 |
| | | | 604/67 |
| 2010/0076400 A1 | | 3/2010 | Wall |
| 2016/0128576 A1 | | 5/2016 | Chiang et al. |
| 2016/0228652 A1 * | | 8/2016 | Cabiri ............... A61M 5/14248 |
| 2016/0256106 A1 | | 9/2016 | Krasnow et al. |
| 2016/0302868 A1 | | 10/2016 | Nagale et al. |
| 2018/0021508 A1 | | 1/2018 | Destefano et al. |

FOREIGN PATENT DOCUMENTS

| | | |
|---|---|---|
| WO | WO-2014/150201 A1 | 9/2014 |
| WO | WO-2015/171777 A1 | 11/2015 |
| WO | WO-2016/003813 A1 | 1/2016 |
| WO | WO-2018/055433 A1 | 3/2018 |
| WO | WO-2018/136398 A1 | 7/2018 |
| WO | WO-2019/081947 A1 | 5/2019 |

OTHER PUBLICATIONS

International Application No. PCT/US2019/057370, International Search Report and Written Opinion, dated Jan. 27, 2020.
International Application No. PCT/US2019/056073, International Search Report and Written Opinion, dated Feb. 3, 2020.

* cited by examiner

DRUG DELIVERY DEVICES WITH PARTIAL DRUG DELIVERY MEMBER RETRACTION

CROSS-REFERENCE TO RELATED APPLICATIONS

This is the United States national phase of International Patent Application No. PCT/US19/55010, filed Oct. 7, 2019, which claims priority to U.S. Provisional Patent Application No. 62/754,402, filed Nov. 1, 2018, the entire contents of each of which are hereby incorporated by reference herein.

FIELD OF DISCLOSURE

The present disclosure generally relates to drug delivery devices and, more particularly, to drug delivery member insertion mechanisms for drug delivery devices.

BACKGROUND

Drugs can be administered through the use of drug delivery devices such as autoinjectors or on-body injectors, which are also referred to as wearable injectors. Autoinjectors and on-body injectors may be used to help automate the injection and delivery or administration process, thereby simplifying the process for certain patient groups or subgroups for which use of the syringe/vial combination or pre-filled syringe systems would be disadvantageous, whether because of physiological or psychological impediments.

Subcutaneous injection is one method for a gradual release of drug product into the blood stream and is the injection type in most autoinjector and on-body injector drug delivery devices. The limited amount of blood vessels and fluid paths within the subcutaneous tissue, however, can cause a pressure build up at the point of injection. This pressure can resist the injection, can cause significant variability in the injection time, and may cause pain for the patients.

SUMMARY

In accordance with a first aspect, a drug delivery device is disclosed that includes a primary container assembly with a reservoir, a plunger stopper disposed within the reservoir, and a drug delivery member coupled to the reservoir by a fluid flow path. The drug delivery device further includes an insertion drive that is operably coupled to the primary container assembly to insert the drug delivery member in a first direction to a subcutaneous location in an insertion operation and a magnetic actuator that is coupled to the primary container assembly and includes a shaft and a circuit with a coil encircling the shaft. A drug dispensing assembly of the drug delivery device includes a plunger rod and a drive operably coupled to the plunger rod to drive the plunger stopper through the reservoir with the plunger rod in a drug dispensing operation. A force sensor is coupled to the drug dispensing assembly and is configured to measure force data associated with dispensing a drug from the reservoir through the drug delivery member to an injection cavity at the subcutaneous location and a controller is in communication with the force sensor and the magnetic actuator. The controller is configured to direct power to the magnetic actuator to translate the shaft linearly through the coil in a second direction to partially retract the drug delivery member in response to a determination that the force data indicates a force greater than or equal to a predetermined threshold.

According to some versions, the drug delivery device can further include one or more of the following aspects: the force sensor can be disposed between the plunger rod and the plunger stopper; the controller can be configured to continuously monitor the force data and direct power to the magnetic actuator based on the force data to control an onset, rate, and extent of retraction of the drug delivery member to maintain a desired tissue resistive pressure in the injection cavity; the controller can be in communication with the drive of the drug dispensing assembly and configured to control operation of the drive and magnetic actuator to maintain a desired drug dispensing force; the magnetic actuator can be the insertion drive; the primary container assembly can include a cannula coaxially disposed over the drug delivery member and fluidly coupled to the reservoir by the flow path and components of the primary container assembly and drug dispensing assembly can be disposed in a generally horizontal plane and the drug delivery member and cannula can extend along an axis generally perpendicular to the horizontal plane; components of the primary container assembly and drug dispensing assembly can be disposed along a longitudinal axis and the flow path can be a hub rigidly coupling the drug delivery member to the reservoir; the drug delivery device can further include a limit stop that is disposed in a path of the shaft of the magnetic actuator to provide a movement limit for the shaft in the second direction; the drug delivery device can further include a lock that is selectively securable to the shaft of the magnetic actuator to retain the shaft and hold the drug delivery member in a retracted position; or the controller can be configured to direct power to the magnetic actuator to retract the drug delivery member after the drug delivery member is inserted to the subcutaneous location.

In accordance with a second aspect, a method for operating a drug delivery device is disclosed herein that includes directing operating an insertion mechanism operably coupled to a primary container assembly with a controller to insert a drug delivery member to a subcutaneous location, operating a drive with the controller to drive a plunger stopper through a reservoir with a plunger rod, measuring force data associated with dispensing a drug from the reservoir through the drug delivery member to an injection cavity at the subcutaneous location with a force sensor coupled to a drug dispensing assembly, determining with the controller whether the force data indicates a force greater than or equal to a predetermined threshold, and directing power to a magnetic actuator operably coupled to the primary container assembly with the controller to translate a shaft of the magnetic actuator linearly through a coil of the magnetic actuator to partially retract the drug delivery member in response to determining that the force data indicates that a force greater than or equal to the predetermined threshold.

According to some versions, the method can include one or more of the following aspects: measuring the force data can include measuring force data with a force sensor disposed between the plunger rod and the plunger stopper; the method can include continuously monitoring the force data with the controller and directing power to the magnetic actuator with the controller based on the force data to control an onset, rate, and extent of retraction of the drug delivery member to maintain a desired tissue resistive pressure in the injection cavity; operating the insertion mechanism can include directing power to the magnetic actuator; operating the insertion mechanism to insert the drug delivery member to the subcutaneous location can include operating the insertion mechanism to insert a cannula to the subcutaneous location; the flow path can be a hub rigidly coupling the drug delivery member to the reservoir and operating the insertion mechanism to insert the drug delivery member to the subcutaneous location can include operating the insertion mechanism to drive the reservoir to insert the drug delivery member to the subcutaneous location; the method can include limiting movement of the shaft of the magnetic actuator in the second direction with a limit stop; the method can include restraining movement of the shaft of the magnetic actuator with a lock to retain the drug delivery member in a retracted position; or the method can include directing power to the magnetic actuator with the controller to retract the drug delivery member after the drug delivery member is inserted to the subcutaneous location.

BRIEF DESCRIPTION OF THE DRAWINGS

The above needs are at least partially met through provision of the embodiments described in the following detailed description, particularly when studied in conjunction with the drawings, wherein.

DETAILED DESCRIPTION

Methods, devices, and components are provided to reduce tissue resistive pressure during a subcutaneous drug delivery operation by increasing the size of the injection cavity by partially retracting a drug delivery member (e.g., a rigid needle or soft cannula) after inserting the same to a subcutaneous position. An injection cavity refers to the cavity at the tip of the drug delivery member inside the patient tissue. The drug delivery devices described herein include a magnetic actuator coupled to the drug delivery member and controlled by a controller. A force sensor can be coupled to drug dispensing components of the devices so that the controller can selectively supply power to the magnetic actuator to retract the drug delivery member based on force data from the sensor. If desired, the controller can vary the amount of power supplied to the magnetic actuator based on the magnitude of the force data to control the extent of drug delivery member retraction. The drug delivery devices can include locks and/or hard stops to contain movement of the drug delivery member.

Figure 1:
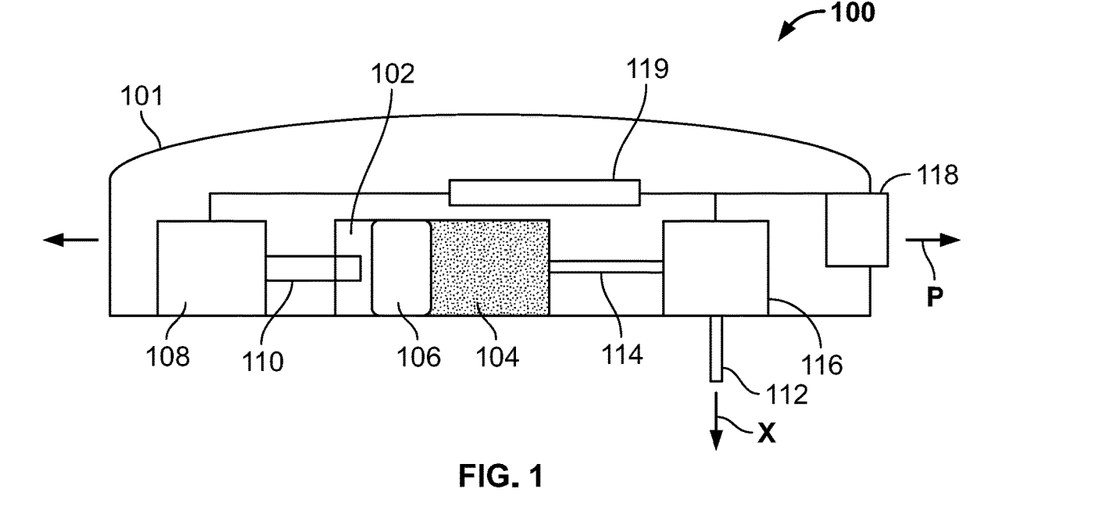
FIG. 1 is a diagrammatic view of an on-body drug delivery device in accordance with various embodiments.

In some versions, as illustrated in FIG. 1, drug delivery devices 100, such as on body injectors, can have a horizontally oriented configuration with drug delivery components disposed generally along a horizontal plane P within a low profile housing 101 of the devices 100. The drug delivery components can include a reservoir 102 having a drug 104 contained therein, a plunger stopper 106 disposed within the reservoir 102 and sildably movable therein along the horizontal plane P, a drive mechanism 108 coupled to a plunger rod 110 to drive the plunger stopper 106 through the reservoir 102, a trocar 112 and drug delivery member 113 which in the depicted version includes a soft cannula oriented along an axis X that extends generally perpendicular to the horizontal plane P, a flow path 114 fluidly coupling the reservoir 102 to the drug delivery member 113, and an insertion mechanism 116 configured to insert the trocar 112 and drug delivery member 113 into a subcutaneous injection region within the user. Thereafter, the insertion mechanism 116 can fully retract the trocar 112 to leave the drug delivery member 113 within the patient at the subcutaneous injection region.

As commonly configured, one or more of the components of the device 100, such as the drive mechanism 108 and insertion mechanism 116, can be operable in response to actuation of a user input device 118 accessible on an exterior of the housing 101. Suitable drive/insertion mechanisms include, but are not limited to, springs, gas sources, phase changing materials, motors, or other electromechanical systems. The device 100 can also include electronic components, such as a controller 119, to control operation of one or more of the drug delivery components. As used herein, a controller will be understood to include a processor and a memory storing logic that is executable by the processor. More specifically, the memory may include one or more tangible non-transitory readable memories having logic (e.g., executable instructions) stored thereon, which instructions when executed by the processor may cause the at least one processor to carry out the actions that the controller is adapted to perform. Additionally, the controller may include other circuitry for carrying out certain actions in accordance with the principles of the present disclosure. Example on body injector devices are described in U.S. Ser. No. 62/536,911, filed Jul. 25, 2017, which is hereby incorporated by reference herein.

Figure 2:
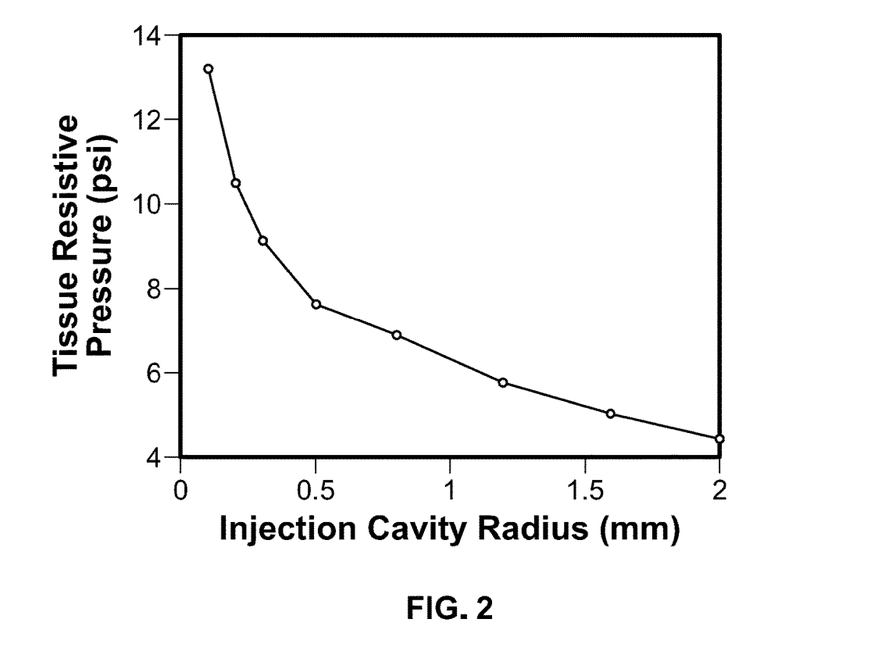
FIG. 2 is a graph showing simulation results for the variation of steady state tissue resistive pressure as a function of the injection cavity radius.

It has been found through simulations based on a developed de novo model of the flow of drug product within the subcutaneous tissue, that the magnitude of the tissue resistive pressure, in addition to drug product viscosity and injection rate, depends on the volume of the injection cavity at the point of injection. Simulation results for the variation of the steady state tissue resistive pressure as a function of the injection cavity radius is shown in FIG. 2. The simulation utilized a drug product viscosity of 10 cP and an injection rate of 6.0 mL/min. The horizontal axis is the diameter of the injection cavity in mm and the vertical axis is the tissue resistive pressure in psi. As shown, the simulation results demonstrate that increasing the size of the injection cavity increase the size of the injection cavity and therefore reduces the tissue resistive pressure against the injection.

Figure 3:
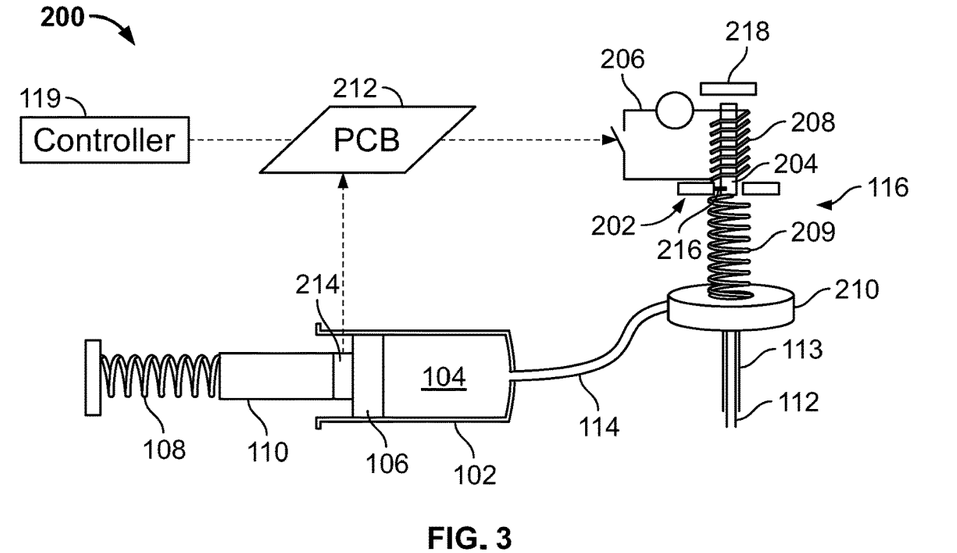
FIG. 3 is a diagrammatic view of an example retraction assembly for a drug delivery device in accordance with various embodiments.

An example assembly 200 for implementing a partial retraction to reduce the tissue resistive pressure within a patient is shown in FIG. 3 with a retraction drive. The assembly 200 is shown in a diagrammatic form for simplicity and ease of showing interacting components configured to cause the partial retraction. As shown, similar to the above form, each assembly 200 includes a reservoir 102 containing a drug 104, a plunger stopper 106 disposed within the reservoir 102, a drive mechanism 108, a plunger rod/piston 110, and a flow path 114 fluidly coupling the reservoir 102 to a drug delivery member 113. In this form, the insertion mechanism 116 includes a drive 209, a spring in the illustrated form, and a magnetic actuator 202. As shown, the magnetic actuator 202 includes a shaft 204 and an electrical circuit 206 with a coil 208 encircling the shaft 204. The spring 209 and the shaft 204 are coupled or mounted to one or more hubs 210 having the trocar 112 and drug delivery member 113 coupled thereto along with the flow path 114.

If desired, the spring 209 can coaxially extend around the shaft 204. In addition to providing a drive for inserting the trocar 112 and drug delivery member 113 to a subcutaneous location, the spring 209 can act as a dampener for movement of the shaft 204 while retracting the trocar 112 and/or drug delivery member 113. In an alternative form, the magnetic actuator 202 can act as the drive for the insertion mechanism 116. In other forms, the drive 209 can be a gas source, phase changing materials, a motor, or other electromechanical system.

The controller 119 is in communication with the drive 209 to selectively cause the spring to be released from a compressed state to drive movement of the trocar 112 and cannula 113 along the x axis to a subcutaneous position within a patient. The controller can also be in communication with the circuit 206 to direct power therethrough to cause the shaft 204 to translate linearly with respect to the coil 208. The assembly 202 can further include a circuit board 212 in communication with a force sensor 214 disposed between the plunger rod 110 and the plunger stopper 106.

As discussed above, when a user actuates the user input 118, the controller 119 directs the drive 209 to drive movement of the trocar 112 and drug delivery member 113 along the x axis to drive the trocar 112 and drug delivery member 113 to a subcutaneous injection region within a patient. In an alternative form, the controller can direct a current to the circuit 206 and through the coil 208, which causes the shaft 204 to translate along the x axis and drive the trocar 112 and drug delivery member 113 to the subcutaneous injection region.

After the insertion operation, in a first retraction operation, the controller 119 can operate the drive 209, if capable of causing the trocar 112 and/or drug delivery member 113 to move in a second, opposite direction, or can direct a current through the circuit 206 to cause the shaft 204 to translate in the second direction along the x axis to partially retract the trocar 112 and/or drug delivery member 113 to reduce tissue resistive pressure in the injection cavity due to the initial insertion. Although the same drive 209 is shown performing the insertion and, optionally, the retraction, a separate retraction drive, having any of the above forms, can be coupled to one or more of the syringe components.

The retraction operation can be performed automatically by the controller 119. In another approach, the retraction operation can be performed in response to reception of a signal in response to a sensed event. The signal can be provided by the user input 118 in response to a user actuation to relieve pressure in the injection cavity, or by a sensor coupled to one or more components of the device 100. For example, the sensor can be a pressure sensor coupled to the flow path 114, a force sensor coupled to a drive, an optical or capacitance sensor to ensure proper location of the device 100 on the patient, an accelerometer to ensure proper orientation of the device 100, and so forth. In an alternative approach, the controller 119 can operate after a predetermined delay from an event. In some examples, the event can be the initial actuation or subsequent actuation of the user input 118, the insertion mechanism 116 starting or finishing the insertion, or the drive mechanism 108 starting the drug dispensing operation.

Thereafter, the controller 119 can operate the drive mechanism 108 or cause the drive mechanism 108 to be released to drive movement of the plunger 110 and plunger stopper 106 to thereby dispense the drug 104 through the trocar 112 and drug delivery member 113. The controller 119 is in communication with the force sensor 214 to receive data regarding the force required to push the plunger stopper 106 through the reservoir 102 to dispense the drug 104 into the injection cavity. In some versions, the controller 119 can estimate a tissue resistive pressure based on the insertion force and determine a predetermined distance for the retraction based on the tissue resistive pressure and direct power to the magnetic actuator accordingly.

Advantageously, if desired, the controller 119 can monitor the force data for a predetermined threshold corresponding to an undesirable tissue resistive pressure within the injection cavity. In response to determining that the force data indicates that the tissue resistive pressure is equal to or greater than the predetermined threshold, the control 119 can direct a current to the circuit 206 to shift the shaft 204 in the second direction to partially retract the trocar 112 and/or drug delivery member 113 to thereby reduce the tissue resistive pressure in the injection cavity. The force feedback can be a dynamic feedback loop, such that the controller 119 can continuously monitor the force and control the onset, rate, and/or extent of the retraction to maintain a desired tissue resistive pressure in the injection cavity.

As shown in FIG. 3, the assembly 200 can include structure to limit or stop undesirable movement of the shaft 204. For example, the assembly 200 can include one or more locks 216, which can be mechanical, to engage and hold the shaft 204, and therefore the trocar 112 and/or drug delivery member 113, in the retracted position. The locks 216 can be configured to automatically engage in response to the shaft 204 translating a predetermined distance, in response to a signal from the controller 119, or combinations thereof. The assembly 200 can also include an upper limit 218 provided by a lock or stationary surface to prevent further movement of the shaft 204 in the second direction to ensure that the trocar 112 and/or drug delivery member 113 is retained within the injection cavity.

Figure 4:
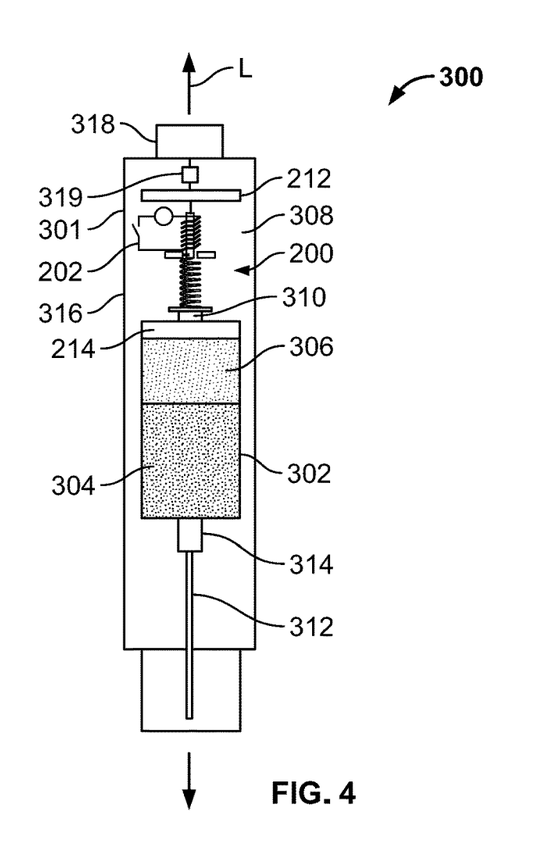
FIG. 4 is a diagrammatic view of an autoinjector drug delivery device in accordance with various embodiments.

In other versions as illustrated in FIG. 4, autoinjector drug delivery devices 300 can have a vertically oriented configuration with some or all drug delivery components disposed in stacked relation along a longitudinal axis L within a housing 301 of the devices 300. More specifically, the devices 300 can be configured to operate and inject a user with the device 300 oriented generally perpendicular to a skin surface of the user. The drug delivery components can include a primary container assembly such as a syringe with a reservoir 302 having a drug 304 contained therein, a plunger stopper 306 disposed within the reservoir 302 and sildably movable therein along the longitudinal axis L, a drug delivery member 312 oriented along the longitudinal axis L, and a flow path or hub 314 fluidly coupling the reservoir 302 to the drug delivery member 312. In some versions, the drug delivery member 312 of the autoinjector of FIG. 4 include a rigid hollow needle. The drug delivery components further include a drive mechanism 308, such as one or more springs, gas sources, phase changing materials, motors, or other electromechanical systems, coupled to a plunger rod 310 to drive the plunger stopper 306 through the reservoir 302 and a needle insertion mechanism 316 configured to insert the drug delivery member 312 to a desired subcutaneous depth within the user. The needle insertion mechanism 316 can be secured to any one of the syringe components.

The device 300 can include electronic components, such as a controller 319, to control operation of one or more of the drug delivery components. Example autoinjector devices are described in U.S. Ser. No. 62/447,174, filed Jan. 17, 2017, which is hereby incorporated by reference herein. If desired, the drive mechanisms 308, 316 can be a single mechanism configured to drive both movement of the plunger stopper 306 and the drug delivery member 312 by moving some or all of the reservoir 302, hub 314, and drug delivery member 312. As commonly configured, one or more of the components of the device 300, such as the drive mechanism 308 and needle insertion mechanism 316, can be operable in response to actuation of a user input device 318 accessible on an exterior of the housing 301.

The above described retraction assembly 200 can also be utilized in these autoinjector devices 300. As shown in FIG. 4, the drug delivery device 300 can include the force sensor 210 disposed between the plunger 310 and the plunger stopper 306 and the controller 319 is in communication with the force sensor 210 and drive mechanisms 308, 316 through the circuit board 208. Similar to the above form, the insertion mechanism 316 can include a drive and the magnetic actuator 202. So configured, when a user actuates the user input 318, the controller 319 operates the drive or directs a current to the circuit 206 to cause the shaft 204 to shift along the longitudinal axis L to drive the drug delivery member 312 to a subcutaneous injection region within a patient. After the insertion operation, in a first retraction operation, the controller 319 can direct a current to the circuit 206 to shift the shaft 204 in the second direction along the longitudinal axis L to partially retract the drug delivery member 312 to reduce tissue resistive pressure in the injection cavity due to the initial insertion. The retraction operation can be performed automatically by the controller 319 or in response to a signal, such as from the user input 318.

Thereafter, the controller 319 can operate the drive mechanism 308 or cause the drive mechanism 308 to be released to drive movement of the plunger rod 310 and plunger stopper 306 to thereby dispense the drug 304 through the drug delivery member 312. The controller 319 is in communication with the force sensor 210 to receive data regarding the force required to push the plunger stopper 306 through the reservoir 302 to dispense the drug 304 into the injection cavity. In some versions, the controller 319 can estimate a tissue resistive pressure based on the insertion force and determine a predetermined distance for the retraction based on the tissue resistive pressure and direct power to the magnetic actuator 202 accordingly.

Advantageously, if desired, the controller 319 can monitor the force data for a predetermined threshold corresponding to an undesirable tissue resistive pressure within the injection cavity. In response to determining that the force data indicates that the tissue resistive pressure is equal to or greater than the predetermined threshold, the control 319 can direct a current to the circuit 206 to cause the shaft 204 to move in the second direction to partially retract the drug delivery member 312 to thereby reduce the tissue resistive pressure in the injection cavity. The force feedback can be a dynamic feedback loop, such that the controller 319 can continuously monitor the force and control the onset, rate, and/or extent of the retraction to maintain a desired tissue resistive pressure in the injection cavity.

The above description describes various assemblies, devices, and methods for use with a drug delivery device. It should be clear that the assemblies, drug delivery devices, or methods can further comprise use of a medicament listed below with the caveat that the following list should neither be considered to be all inclusive nor limiting. The medicament will be contained in a reservoir. In some instances, the reservoir is a primary container that is either filled or pre-filled for treatment with the medicament. The primary container can be a cartridge or a pre-filled syringe.

For example, the drug delivery device or more specifically the reservoir of the device may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgastrim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of sequence identification number 2 as set forth therein in FIG. 2 and/or the heavy chain of sequence identification number 4, as set forth therein in FIG. 4, each of which is individually and specifically incorporated by reference herein in its entirety fully as disclosed in the foregoing publication;

Myostatin binding proteins, peptibodies, and related proteins, and the like, including myostatin specific peptibodies, particularly those described in U.S. Publication No. 2004/0181033 and PCT Publication No. WO 2004/058988, which are incorporated by reference herein in their entirety particularly in parts pertinent to myostatin specific peptibodies, including but not limited to peptibodies of the mTN8-19 family, including those of sequence identification numbers 305-351, including TN8-19-1 through TN8-19-40, TN8-19 con1 and TN8-19 con2; peptibodies of the mL2 family of sequence identification numbers 357-383; the mL15 family of sequence identification numbers 384-409; the mL17 family of sequence identification numbers 410-438; the mL20 family of sequence identification numbers 439-446; the mL21 family of sequence identification numbers 447-452; the mL24 family of sequence identification numbers 453-454; and those of sequence identification numbers 615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publication No. 2004/097712, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned publication;

Ang2 specific antibodies, peptibodies, and related proteins, and the like, including but not limited to those described in PCT Publication No. WO 03/057134 and U.S. Publication No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2×L1(N); 2×L1(N) WT; Con4 (N), Con4 (N) 1K WT, 2×Con4 (N) 1K; L1C; L1C 1K; 2×L1C; Con4C; Con4C 1K; 2×Con4C 1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publication No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AbIA1; AbIF; AbIK; AbIP; and AbIP, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in U.S. Publication No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing publication;

Also among non-limiting examples of anti-IGF-1R antibodies for use in the methods and compositions of the present invention are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (y4), deposited at the ATCC under number PTA-5214, and a light chain encoded by a polynucleotide in plasmid 15H12/19D12 LCF (K), deposited at the ATCC under number PTA-5220, as described therein; and (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, which are incorporated herein by reference in their entireties as to such antibodies and related proteins, including but not limited to antibodies designated therein as follow: 16H (having light chain variable and heavy chain variable sequences designated therein as, respectively, sequence identification number 1 and sequence identification number 7); 5D (having light chain variable and heavy chain variable sequences designated therein as, respectively, sequence identification number 2 and sequence identification number 9); 2H (having light chain variable and heavy chain variable sequences designated therein as, respectively, sequence identification number 3 and sequence identification number 10); 43H (having light chain variable and heavy chain variable sequences designated therein as, respectively, sequence identification number 6 and sequence identification number 14); 41H (having light chain variable and heavy chain variable sequences designated therein as, respectively, sequence identification number 5 and sequence identification number 13); and 15H (having light chain variable and heavy chain variable sequences designated therein as, respectively, sequence identification number 4 and sequence identification number 12), each of which is individually and specifically incorporated by reference herein in its entirety fully as disclosed in the foregoing publication;

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing publication and in Thakur et al. (1999), Mol. Immunol. 36:1107-1115. In addition, description of the properties of these antibodies provided in the foregoing publication is also incorporated by reference herein in its entirety. Specific antibodies include those having the heavy chain of sequence identification number 17 and the light chain of sequence identification number 18; those having the heavy chain variable region of sequence identification number 6 and the light chain variable region of sequence identification number 8; those having the heavy chain of sequence identification number 19 and the light chain of sequence identification number 20; those having the heavy chain variable region of sequence identification number 10 and the light chain variable region of sequence identification number 12; those having the heavy chain of sequence identification number 32 and the light chain of sequence identification number 20; those having the heavy chain variable region of sequence identification number 30 and the light chain variable region of sequence identification number 12; those having the heavy chain sequence of sequence identification number 21 and the light chain sequence of sequence identification number 22; those having the heavy chain variable region of sequence identification number 14 and the light chain variable region of sequence identification number 16; those having the heavy chain of sequence identification number 21 and the light chain of sequence identification number 33; and those having the heavy chain variable region of sequence identification number 14 and the light chain variable region of sequence identification number 31, as disclosed in the foregoing publication. A specific antibody contemplated is antibody 1119 as disclosed in the foregoing U.S. publication and having a complete heavy chain of sequence identification number 17 as disclosed therein and having a complete light chain of sequence identification number 18 as disclosed therein;

TALL-1 specific antibodies, peptibodies, and the related proteins, and the like, and other TALL specific binding proteins, such as those described in U.S. Publication Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686,292 and 6,468,529 and in PCT Publication No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in U.S. Publication No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publication No. WO 2006/081171, which is herein incorporated by reference in its entirety, particularly in parts pertinent to proteins that bind amyloid-beta proteins. One antibody contemplated is an antibody having a heavy chain variable region comprising sequence identification number 8 and a light chain variable region having sequence identification number 6 as disclosed in the foregoing publication;

c-Kit specific antibodies, peptibodies, related proteins, and the like, including but not limited to those described in U.S. Publication No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, which is incorporated herein by reference in its entirety, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-05 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgastrim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-α4integrin mAb); Valortim® (MDX-1303, anti-*B. anthracis* protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Rα mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MY0-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Rα mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab), as well as molecules, variants, analogs or derivatives thereof as disclosed in the following patents or patent applications, each of which is herein incorporated by reference in its entirety for all purposes: U.S. Pat. No. 8,030,547, U.S. Publication No. 2013/0064825, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223, 593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Vargehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, bispecific T cell engager (BITE®) antibodies, e.g. BLINCYTO® (blinatumomab), can be used in the device. Alternatively, included can be an APJ large molecule agonist e.g., apelin or analogues thereof in the device. Information relating to such molecules can be found in PCT Publication No. WO 2014/099984.

In certain embodiments, the medicament comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the medicament comprises a therapeutically effective amount of the anti-TSLP antibody designated as A5 within U.S. Pat. No. 7,982,016.

Although the drug delivery devices, methods, and components thereof, have been described in terms of exemplary embodiments, they are not limited thereto. The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent that would still fall within the scope of the claims defining the invention. For example, components described herein with reference to certain kinds of drug delivery devices, such as on-body injector drug delivery devices or other kinds of drug delivery devices, can also be utilized in other kinds of drug delivery devices, such as autoinjector drug delivery devices.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. A drug delivery device comprising:
   a primary container assembly including a reservoir, a plunger stopper disposed within the reservoir, and a drug delivery member fluidly coupled to the reservoir by a flow path;
   an insertion drive operably coupled to the primary container assembly to insert the drug delivery member in a first direction to a subcutaneous location in an insertion operation;
   a magnetic actuator coupled to the primary container assembly and including a shaft and a circuit with a coil encircling the shaft;
   a drug dispensing assembly including a plunger rod and a drive operably coupled to the plunger rod to drive the plunger stopper through the reservoir with the plunger rod in a drug dispensing operation;
   a force sensor coupled to the drug dispensing assembly and configured to measure force data associated with dispensing a drug from the reservoir through the drug delivery member to an injection cavity at the subcutaneous location; and
   a controller in communication with the force sensor and the magnetic actuator, the controller configured to direct power to the magnetic actuator to translate the shaft linearly through the coil in a second direction to partially retract the drug delivery member in response to determining that the force data indicates a force greater than or equal to a predetermined threshold.

2. The drug delivery device of claim 1, wherein the force sensor is disposed between the plunger rod and the plunger stopper.

3. The drug delivery device of claim 1, wherein the controller is configured to continuously monitor the force data and direct power to the magnetic actuator based on the force data to control an onset, rate, and extent of retraction of the drug delivery member to maintain a desired tissue resistive pressure in the injection cavity.

4. The drug delivery device of claim 1, wherein the controller is in communication with the drive of the drug dispensing assembly and configured to control operation of the drive and magnetic actuator to maintain a desired drug dispensing force.

5. The drug delivery device of claim 1, wherein the magnetic actuator comprises the insertion drive.

6. The drug delivery device of claim 1, further comprising a trocar and wherein the drug delivery member comprises a cannula coaxially disposed with the trocar and fluidly coupled to the reservoir by the flow path; and components of the primary container assembly and drug dispensing assembly are disposed in a generally horizontal plane and the trocar and cannula extend along an axis generally perpendicular to the horizontal plane.

7. The drug delivery device of claim 1, wherein components of the primary container assembly and drug dispensing assembly are disposed along a longitudinal axis; and the flow path comprises a hub rigidly coupling the drug delivery member to the reservoir.

8. The drug delivery device of claim 1, further comprising a limit stop disposed in a path of the shaft of the magnetic actuator to provide a movement limit for the shaft in the second direction.

9. The drug delivery device of claim 1, further comprising a lock selectively securable to the shaft of the magnetic actuator to retain the shaft and hold the drug delivery member in a retracted position.

10. The drug delivery device of claim 1, wherein the controller is further configured to direct power to the magnetic actuator to retract the drug delivery member after the drug delivery member is inserted to the subcutaneous location.

* * * * *